(12) United States Patent
Denti et al.

(10) Patent No.: US 7,014,637 B1
(45) Date of Patent: Mar. 21, 2006

(54) TAMPON APPLICATOR HAVING INDICATORS

(75) Inventors: Federica Denti, Schwalbach am Taunus (DE); Beate Rosemarie Stellbrink, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/196,662

(22) Filed: Aug. 3, 2005

Related U.S. Application Data

(63) Continuation of application No. 11/040,154, filed on Jan. 21, 2005.

(51) Int. Cl.
*A61M 13/32* (2006.01)

(52) U.S. Cl. .......... 604/904; 604/11; 604/385.01; D24/124; 206/529

(58) Field of Classification Search ........ 604/904, 604/11, 380; D24/124, 126; D3/203.5; 206/529
See application file for complete search history.

(56) References Cited

U.S. PATENT DOCUMENTS

| | | | |
|---|---|---|---|
| 2,123,750 A | | 7/1938 | Schulz |
| 3,643,661 A | * | 2/1972 | Crockford ............ 604/15 |
| 3,738,364 A | | 6/1973 | Brien et al. |
| 3,854,481 A | | 12/1974 | Messing |
| 3,946,737 A | | 3/1976 | Kobler |
| 4,326,527 A | | 4/1982 | Wollangk et al. |
| 4,591,523 A | | 5/1986 | Thompson |
| 4,609,518 A | | 9/1986 | Curro et al. |
| 4,629,643 A | | 12/1986 | Curro et al. |
| 4,685,178 A | | 8/1987 | Nakanishi |
| 4,839,216 A | | 6/1989 | Curro et al. |
| 4,951,368 A | | 8/1990 | Heinen |
| 5,153,971 A | | 10/1992 | Van Iten |
| 5,350,371 A | | 9/1994 | Van Iten |
| 5,395,308 A | * | 3/1995 | Fox et al. ............ 604/15 |
| 5,592,725 A | | 1/1997 | Brinker |
| 5,788,910 A | | 8/1998 | McNelis et al. |
| 5,832,576 A | | 11/1998 | Leutwyler et al. |
| 5,865,322 A | * | 2/1999 | Miller ............ 211/49.1 |
| 5,891,081 A | | 4/1999 | McNelis et al. |
| 5,911,712 A | | 6/1999 | Leutwyler et al. |
| 5,958,321 A | | 9/1999 | Schoelling et al. |
| 6,003,216 A | | 12/1999 | Hull, Jr. et al. |

(Continued)

FOREIGN PATENT DOCUMENTS

EP 0 422 660 B1 2/1994

(Continued)

*Primary Examiner*—Tatyana Zalukaeva
*Assistant Examiner*—Laura C Hill
(74) *Attorney, Agent, or Firm*—Ingrid N. Hickman; Kevin C. Johnson; Steven W. Miller

(57) ABSTRACT

An array of disposable absorbent articles. The array has a first absorbent article and a second absorbent article. The first absorbent article is enclosed in a first tampon applicator having i.) an outer surface wherein the outer surface has an outer surface area and ii.) a first identifier having a first surface area. The first identifier is disposed on the first absorbent article and corresponds to a first absorbency. The first identifier is disposed on the first absorbent article. A second absorbent article is enclosed in a second tampon applicator having i.) an outer surface wherein the outer surface has an outer surface area and ii.) a second identifier having a second surface area. The second identifier is disposed on the second absorbent article and corresponds to a second absorbency. The first surface area is different than the second surface area.

17 Claims, 4 Drawing Sheets

U.S. PATENT DOCUMENTS

| | | |
|---|---|---|
| 6,039,716 A * | 3/2000 | Jessup et al. ........... 604/385.18 |
| 6,071,259 A | 6/2000 | Steiger et al. |
| 6,156,021 A | 12/2000 | Tojkander |
| 6,283,952 B1 | 9/2001 | Child et al. |
| 6,310,269 B1 | 10/2001 | Friese et al. |
| 6,601,705 B1 | 8/2003 | Molina et al. |
| 6,939,340 B1 * | 9/2005 | Berges ................... 604/385.01 |
| 2002/0151859 A1 | 10/2002 | Schoelling |
| 2002/0183681 A1 * | 12/2002 | Bernard ........................ 604/15 |
| 2003/0055393 A1 * | 3/2003 | Stults et al. ............ 604/385.17 |
| 2004/0030316 A1 * | 2/2004 | Gubernick et al. ......... 604/383 |
| 2004/0143231 A1 * | 7/2004 | Nair et al. ............. 604/385.01 |
| 2005/0055393 A1 * | 3/2005 | Cole et al. ............. 604/385.01 |

FOREIGN PATENT DOCUMENTS

| | | |
|---|---|---|
| WO | WO 00/37013 A1 | 6/2000 |
| WO | WO 01/66055 A1 | 9/2001 |
| WO | WO 02/078586 A3 | 10/2002 |

* cited by examiner

TAMPON APPLICATOR HAVING INDICATORS

CROSS REFERENCE TO RELATED APPLICATION

This application is a continuation of U.S. application Ser. No. 11/040,154 filed Jan. 21, 2005.

FIELD OF THE INVENTION

This invention relates to tampon applicators, and more particularly to tampons applicators comprising an indicator.

BACKGROUND OF THE INVENTION

Surprisingly, some of the problems associated with the proper selection and use of such products are traceable to modern developments in the technologies used to improve their performance. In the past, the absorbency of catamenials, as well as other absorbent articles such as tampons, baby diapers, and adult incontinence garments, could be estimated by visual inspection of their size, shape, and bulk. However, improvements made in modern absorbent articles in an effort to increase in-use comfort and to increase the compactness for ease-of-packaging have resulted in the development of thin, and even ultra-thin, products. Rather than relying on size and bulk to achieve absorbency, such modern articles typically employ absorbent gelling materials (hereinafter "AGM"; "superabsorbents"), new methods of forming absorbent batts or pads of cellulosic fibers, and/or various structural improvements to achieve the desired absorbency. Whatever the technology, the result is that the performance or absorbent capacity of such articles can no longer be reliably judged solely on the basis of their size and bulk.

In addition to improvements in technology, improvements made in modern absorbent articles in an effort to increase in-use comfort and consumer satisfaction have resulted in the proliferation of sizes, shapes, conformations and brands in the field of disposable absorbent articles such as feminine care articles. Because of the proliferation of sizes, shapes, conformations and brands in the field of disposable absorbent articles, customers have difficulty differentiating between the many types of articles and the variations of article characterizations within these article types. In other words, differentiation and selection of absorbent articles is difficult due to the many types of articles and variations of article characterizations within these article types. For example, differentiation and selection of catamenial articles are particularly difficult due to the many choices of article absorbencies such as: light absorbency, regular absorbency, and extra absorbency and article configurations, for example, daytime articles, nighttime articles, winged versions and the like. Differentiation and selection of articles is also particularly difficult when there is not any artwork, color, and/or shape which differentiates each type of absorbent article.

Often color is used to convey a particular performance characteristic of a given article. For example, at least one manufacturer of catamenial tampon applicator uses color-based signals on both the outer packaging and the wrapper of such tampon applicators to denote absorbent capacity. In such articles, different colors are used to represent different article characteristic levels (in this case absorbency). For example, a green band on the package and wrapper of a tampon applicator might signal a "super" absorbency tampon, while a blue band might signal a "regular" absorbency tampon.

However, it is problematic when the tampon applicator is removed from the wrapper and/or package and there is not any indication of the type of product absorbency. Thus, there is a need for an intuitive method of signaling to the user the absorbency which is independent of the packaging and/or wrapper when the tampon applicator is then removed from the original container and placed in the bathroom drawer, purse, etc.

Proper selection of consumer articles requires an explicit signal. Despite considerable attention being given to such matters, mistakes continue to be made by consumers. In some instances, the consumer may be inattentative to the packaging which signals the absorbency or unable to determine the thinness or thickness of the article, or may have a limited amount of time to make a selection of a given article. In others, linguistic difficulties may contribute to improper selection and usage.

Typical instructional matter pertaining to the proper selection and use of absorbent articles conventionally comprises printed text, pictures, diagrams, labels, and combinations thereof located on the package. The objective of any optimal instructional matter is to be univocal, i.e., to convey a message regarding proper selection and usage in such a clear, concise, and exact manner that essentially any user, regardless of the package or wrapper, is prompted to choose and employ the article correctly.

Accordingly, the proper usage of extra, regular, or light capacity absorbent articles begins with the proper selection of such articles independent of the package and/or wrapper. The present invention provides an easy and intuitive signal for selecting the proper absorbency, which provides a consumer benefit and ensures that the right article is chosen.

SUMMARY OF THE INVENTION

The present invention relates to an array of disposable tampon applicators. The array comprises a first tampon applicator and a second tampon applicator. The first tampon applicator has i.) an outer surface wherein the outer surface has an outer surface area and ii.) a first identifier having a first surface area. The first identifier is disposed on the first tampon applicator and corresponds to a first absorbency. The second tampon applicator has i.) an outer surface wherein the outer surface has an outer surface area and ii.) a second identifier having a second surface area. The second identifier is disposed on the second tampon applicator and corresponds to a second absorbency. The first surface area of the first tampon applicator is different than the second surface area of the second absorbent article.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

DETAILED DESCRIPTION OF THE INVENTION

Figure 1:
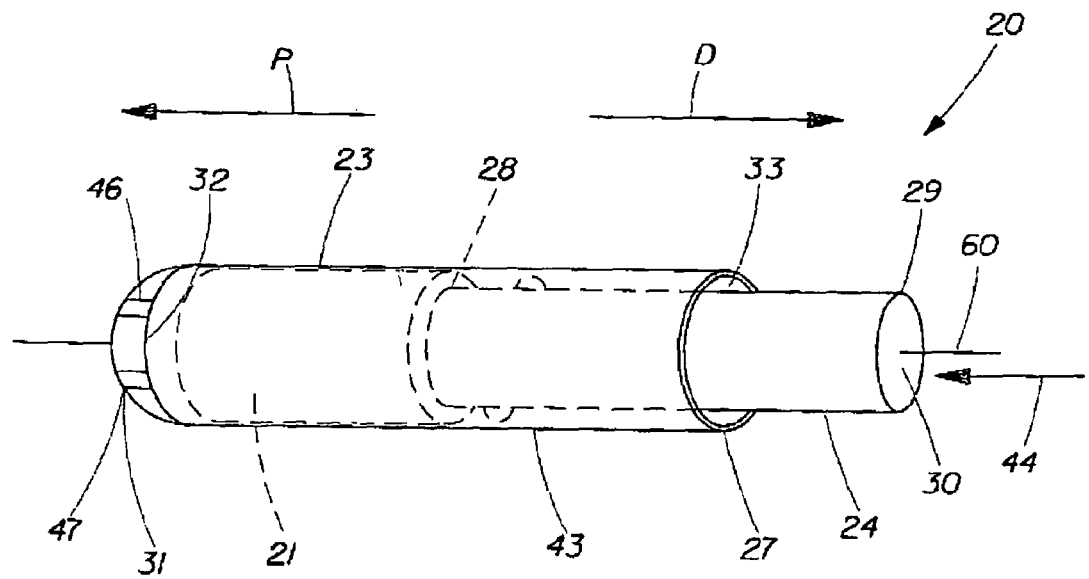
FIG. 1 is a perspective view along a longitudinal axis of a tampon applicator of the present invention.

Section A will provide terms which will assist the reader in best understanding the features of the invention but not to introduce limitations in the terms inconsistent with the context in which they are used in this specification. These definitions are not intended to be limiting. Section B will discuss the tampon of the present invention.

A. Terms

The following are terms which will assist the reader in best understanding the features of the invention, but do not introduce limitations in the terms inconsistent with the context in which they are used in this specification. These definitions are not intended to be limiting.

"Absorbent articles" as referred to herein are primarily sanitary napkins, sanitary panties, interlabial devices, intravaginal devices (tampons), adult incontinence products, infant diapers, pantiliners, and the like. Theses articles have been described in the extensive patent literature and many such articles are in the stream of commerce. See, for example, for sanitary napkins, U.S. Pat. No. 4,463,045 issued to Ahr et al. and U.S. Pat. No. 4,556,146 issued to Swanson et al.; for tampons, U.S. Pat. No. 5,087,239 issued to Beastall et al. and U.S. Pat. No. 5,279,541 issued to Frayman et al.; and for diapers, U.S. Pat. No. 4,573,986 issued to Minetola et al.; U.S. Pat. No. 4,695,278 issued to Lawson; U.S. Pat. No. 4,081,301 issued to Buell; and U.S. Pat. No. 4,515,595 issued to Kievit. Typically, the disclosed absorbent articles contain an absorbent structure in the form of a "core" or a pad. Various fluid-permeable topsheets, fluid-impermeable backsheets, panty-protective "wings," tape fasteners are optionally used to construct elements for such articles and are all within the experience of those of ordinary skill in the art.

The term, "surface area" as used herein refers to the measure of any two-dimensional figure within a 1 cm by 1 cm measured portion, such that two surface areas may be compared relatively to one another. While the measured portion will have a defined dimension, the surface area within that portion will always be different from the defined dimension if the tampon has topographical features such as protuberances, depressions, and grooves present within the measured portion. Any known method may be used so long as the measurement does not alter or otherwise distort the surface area, such as by swelling the materials. The preferred method of measure involves image analysis using any image analysis software or algorithm for assessing surface area. It should be understood that the surface area of interest is that which is apparent at the millimeter scale using light microscopy or macrophotography. As well, it should be noted that the surface area is not at the molecular or atomic scale, e.g. techniques such as AFM or BET are not useful herein.

As used herein, "tampon applicator" refers to a device or implement that facilitates the insertion of a tampon, medicament, treatment device, visualization aid, or other into an external orifice of a mammal, such as the vagina, rectum, ear canal, nasal canal, or throat. Non-limiting specific examples of such include any known hygienically designed applicator that is capable of receiving a tampon may be used for insertion of a tampon, including the so-called telescoping, tube and plunger, and the compact applicators, an applicator for providing medicament to an area for prophylaxis or treatment of disease, a spectroscope containing a microcamera in the tip connected via fiber optics, a speculum of any design, a tongue depressor, a tube for examining the ear canal, a narrow hollow pipe for guiding surgical instruments, and the like.

As used herein, "indicator" refers to a signal perceptible to the user that corresponds to a functionally distinguishable characteristic of a feminine hygiene article. In a system of products, the functionally-distinguishable characteristic of a feminine hygiene article is a characteristic that is different in surface area from other products in the same array. The indicator can be any indicia and/or shape. As used herein, indicia is any identifying marking, which may include words and/or graphics identifying the product in use.

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

As used herein, the term "density" is used with its common technical meaning with units of $g/cm^3$ or g/cc. The density may refer specifically to that of a specific region or feature of the tampon as noted. The density will be measured, unless otherwise noted, by taking the weight divided by the geometric volume described by the shape. Unless noted, density refers to that of the overall structure and not the individual components, and will include in the measurement void volume of small pores and voids within the overall structure.

The term "digital tampon" refers to a tampon which is intended to be inserted into the vaginal canal with the user's finger and without the aid of an applicator. Thus, digital tampons are typically visible to the consumer prior to use rather than being housed in an applicator.

The term "folded" as used herein, is the configuration of the tampon pledget that may be incidental to lateral compaction of the absorbent material or may purposely occur prior to a compression step. Such a configuration is readily recognizable, for example, when the absorbent material abruptly changes direction such that one part of the absorbent material bends and lies over another part of the absorbent material.

As used herein, "generally cylindrical" refers to the usual shape of tampons as is well known in the art, but which also includes oblate or partially flattened cylinders, curved cylinders, and shapes which have varying cross-sectional areas (such as a Coke™ bottle shape). The longitudinal axis refers to the longest linear dimension of the tampon. The cross-section refers to a slice taken at right angles to the longitudinal axis.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

Figure 2:
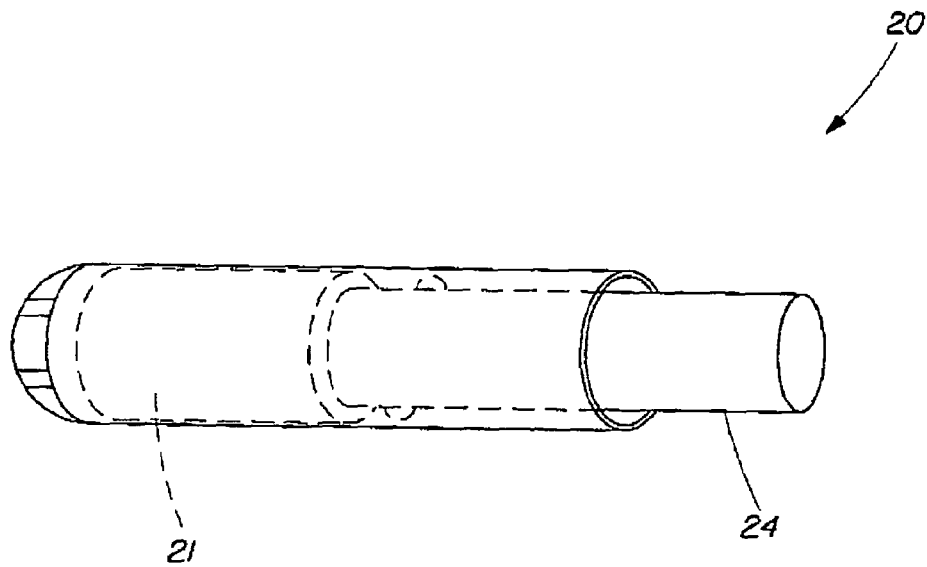
FIG. 2 is a perspective view of the tampon applicator of the present invention.

As used herein, the term "longitudinal axis" of a tampon refers to the axis that runs through the center of the tampon as shown in FIG. 2. A portion of the tampon may be asymmetric about the longitudinal axis, such as when the withdrawal end region is flared and distorted from the original shape of the rest of the tampon (such as a "fin shape"). Further, the longitudinal axis may be linear or non-linear.

The "outer surface" of a tampon applicator refers to the visible surface of the tampon applicator. At least part of the outer surface may be smooth or alternatively may have topographic features, such as ribs, spiraling ribs, a mesh pattern, or other topographical features.

The "outer surface" of a tampon applicator refers to the visible surface of the (compressed and/or shaped) tampon applicator prior to use and/or expansion. At least part of the outer surface may be smooth or alternatively may have topographic features, such as ribs, spiraling ribs, a mesh pattern, or other topographical features.

The term "cross-section," as used herein, is any 5 mm thick section orthogonal to the longitudinal axis.

As used herein, the terms "pledger" or "tampon pledget" are intended to be interchangeable and refer to a construction of absorbent material prior to the compression and/or shaping of such construction into a tampon as described above. Pledgets may be rolled, folded or otherwise manipulated prior to compression. Tampon pledgets are sometimes referred to as tampon blanks, or a softwinds, and the term "pledget" is intended to include such terms as well. In general in this specification, the term "tampon" is used to refer to a finished tampon after the compression and/or shaping process. It will be recognized by those of skill in the art that in some contexts these terms are interchangeable. The different stages of tampon manufacture are described herein with an eye toward providing the greatest possible clarity. Therefore, the terms used are to assist the reader in best understanding the features of the invention and not to introduce limitations in the terms not consistent with the context in which they are used in this specification.

As used herein, a tampon has a "self-sustaining shape" when a tampon pledget has been compressed and/or shaped such that it assumes a general shape and size, which is vaginally insertable, absent external forces. It will be understood by one of skill in the art that this self-sustaining shape need not, and preferably does not persist during actual use of the tampon. That is, once the tampon is inserted and begins to acquire fluid, the tampon may begin to expand and may lose its self-sustaining form.

As used herein, the term "tampon" refers to any type of absorbent structure that can be inserted into the vaginal cavity or other body cavities for the absorption of fluid therefrom or for the delivery of active materials, such as medicaments or moisture. A tampon can be straight or non-linear in shape, such as curved along the longitudinal axis.

Generally, there are two types of tampons. The first type of tampon is a self-sustaining tampon. Tampons are generally "self-sustaining" in that they will tend to retain their general shape and size before use. A typical self-sustaining tampon is 35–60 mm long, the length measured from the top of the tampon to the base of the tampon along a longitudinal axis. The measurement to the base of the tampon does not include any overwrap, secondary absorbent member, or withdrawal cord which extends beyond the tampon's main absorbent material. A typical self-sustaining tampon is 5–20 mm wide corresponding to the largest cylindrical cross section. The width can vary along the length of the self-sustaining tampon.

The second type of tampon is an easily "deformable, fluid-permeable bag tampon". The deformable, fluid-permeable bag tampon consists of, but is not limited to, pieces such as absorbent chips, spheres, or fibers such that the fluid permeable bag tampon is readily deformable with a force of less than about 3 psi. The tampon is substantially deformable at pressures of less than about 1 psi; resulting in the tampon spreading or being easily indented when the pressure is applied from a surface of about 0.15 mm diameter.

As used herein, the terms "vaginal cavity" and "within the vagina" refer to the internal genitalia of the human female in the pudendal region of the body.

B. General Descprition of Basis Parts of a Tampon Applicator

Referring to FIG. 1, a tampon applicator 20 is shown which is designed to position tampon 21 inside the vaginal cavity. Also, FIG. 1 shows "proximal" and "distal" designated as P and D, respectively. The tampon applicator 20 may be used with any type of tampon 21. The tampon 21 could be a self-sustaining tampon or a deformable fluid permeable bag tampon.

Generally, the tampon applicator 20 includes an outer member 23 and an inner member 24. The outer member 23 comprises an insertion end 31 and a second end 27 opposed to the insertion end 31. During insertion of the tampon applicator 20 into the body of a wearer, the insertion end 31 is the most proximal end to the body of the wearer along the longitudinal axis 60 and the second end 27 is the most distal end to the body of the wearer along the longitudinal axis 60. A preformed hinge or groove 32 may extend around the periphery of the outer member 23 near the insertion end 31. The outer member 23 may also have a dome-shaped end having a number of radial slits 46 therein extending from a central aperture to the groove 32. The portion of the outer member 23 adjacent to the insertion end 31 may also have an openable end, such as petals 47. In addition, the outer member 23 can contain a grip region 43 located adjacent to the second end 27 of the outer member 23.

The inner member 24 is dimensioned to slidably move within the hollow interior portion 33 of the outer member 23, with minimal clearance therebetween. The inner member 24 has a first end 28 and a second end 29 opposed to the first end 28. The first end 28 is the most proximal end of the inner member 24 along the longitudinal axis 60. In this embodiment, the first end 28 provides the necessary force to expel the (FIG. 3) tampon 21. The second end 29 is the most distal end of the inner member 24 along the longitudinal axis 60. An axial force 44 is applied to the second end 29 of inner member 24 to expel the (FIG. 3) tampon 21. Also, the inner member 24 can have a hollow interior portion 30. Alternatively, the inner member 24 can be solid or partially solid.

The tampon applicator 20 has a pre-expelled state and a partially expelled state. During the pre-expelled state, as is readily seen in FIG. 1, the tampon 21 sits within the outer member 23 and is substantially aligned with the tampon applicator 20. The tampon 21 can remain snugly therein without any outside force to sustain its position in the tampon applicator 20. In one nonlimiting example, the tampon 21 can be enveloped by the inner member 24 or embedded within inner member 24 during expulsion of tampon 21. The tampon 21 may or may not be in contact with the first end 28 of the inner member 24 before expulsion of the tampon 21.

Figure 3:
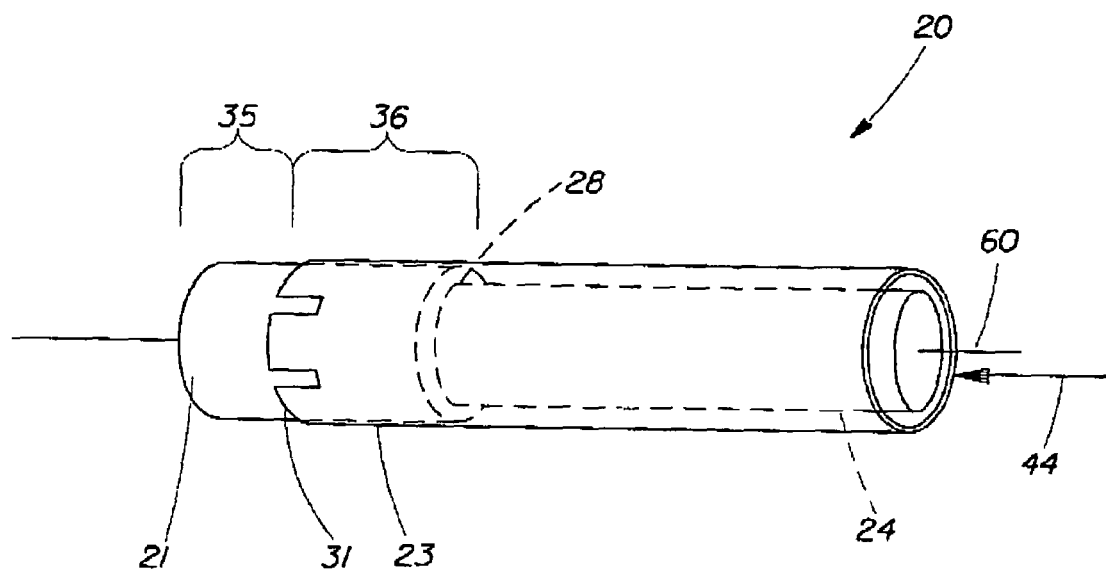
FIG. 3 is a perspective view of the tampon applicator of the present invention when the tampon applicator is fully engaged.

As is readily seen in FIG. 3, when the axial force 44 is applied along the longitudinal axis 60, the inner member 24 slides toward the insertion end 31 of the outer member 23. The inner member 24 bears against the rear end of tampon 21 pushing the tampon 21 toward the insertion end 31 of outer member 23. Upon full engagement of inner member 24 with outer member 23, the exposed portion 35 of the tampon 21 is expelled from the tampon applicator 20 and a remaining portion 36 of the tampon 21 is contained within the tampon applicator 20.

C. Incorporation of Indicators into a Tampon Applicator

The above disclosure is meant to give a general description of the basic parts of feminine hygiene articles such as tampon applicators and the like as they are known in the art. The description is not intended to be limiting. Any and all of various known elements, features and processes of known tampon applicators and the like can be incorporated in the feminine hygiene article of the present invention as desired or needed for particular use benefits. Now, with respect to the remaining disclosure, the novel features and benefits of the present invention will be described.

In its broadest aspect, the present invention is directed to an array of disposable tampon applicators comprising a line-up of disposable tampon applicators in which each disposable tampon applicator comprises an indicator. When so employed, the surface area that the indicator covers provides an easy and intuitive method for indicating the absorbency of the product. When indicators are placed on the tampon applicator, the indicator provides a method for selecting the proper absorbency products independent the package and/or tampon applicator wrapper. Thus, when the article is then removed from the original container and placed in the bathroom drawer, purse, etc. the user can select the proper absorbency product.

By the present invention, a system of distinct indicators is used to implement the proper selection and use of consumer products, including catamenials, especially tampon applicators, tampons, sanitary napkins, and interlabial devices. The present invention may also be used in other fields such as beauty care, food and beverage, health care, laundry and cleaning, and tissues and towels. For example, indicators may be used in beauty care to denote product performance characteristics such as more or less moisture; in coffee products to differentiate between light, medium, and dark roast levels; in the health care area to denote stronger medicine such as cough drops and chloraseptics; in laundry and cleaning to indicate a higher concentration of detergent; and in tissues and towels to denote levels of absorbency. The use of indictors in this manner univocally and unequivocally connotes performance characteristics, thereby improving user satisfaction with the product and decreased anxiety in choosing the correct product.

The indicators are perceived and referred to in terms of the amount of surface area that is covered by the tampon applicator. Typically, the more surface area that the indicator covers the greater the absorbency that the indicator indicates. For example, in the context of one embodiment the present invention, a tampon applicator having six grooves signals a "mini" absorbency tampon; a tampon applicator having nine grooves signals a "normal" absorbency tampon; a tampon applicator having twelve grooves signals a "super" absorbency tampon, and a tampon applicator having fifteen grooves signals a "super plus" absorbency tampon. It will be appreciated by those skilled in the visual arts that the number of grooves are relative, not absolute, terms that can be used to compare the surface areas with each other.

With such a line up, the consumer is able to remember easily that less surface area corresponds to lower absorbency while higher absorbency corresponds to a higher surface area. Preferably, the variation in surface area is great enough to be readily perceived by a consumer without having to refer to an external basis or calibration means for comparison. For example, if the product performance characteristic being represented is absorbency, an indicator covering about 24% of the surface area of the tampon applicator might represent low absorbency. An indicator covering about 46% of the surface area of the tampon applicator might represent high absorbency, while an indicator covering about 41% of the surface area of the tampon applicator might represent regular absorbency.

Figure 4:
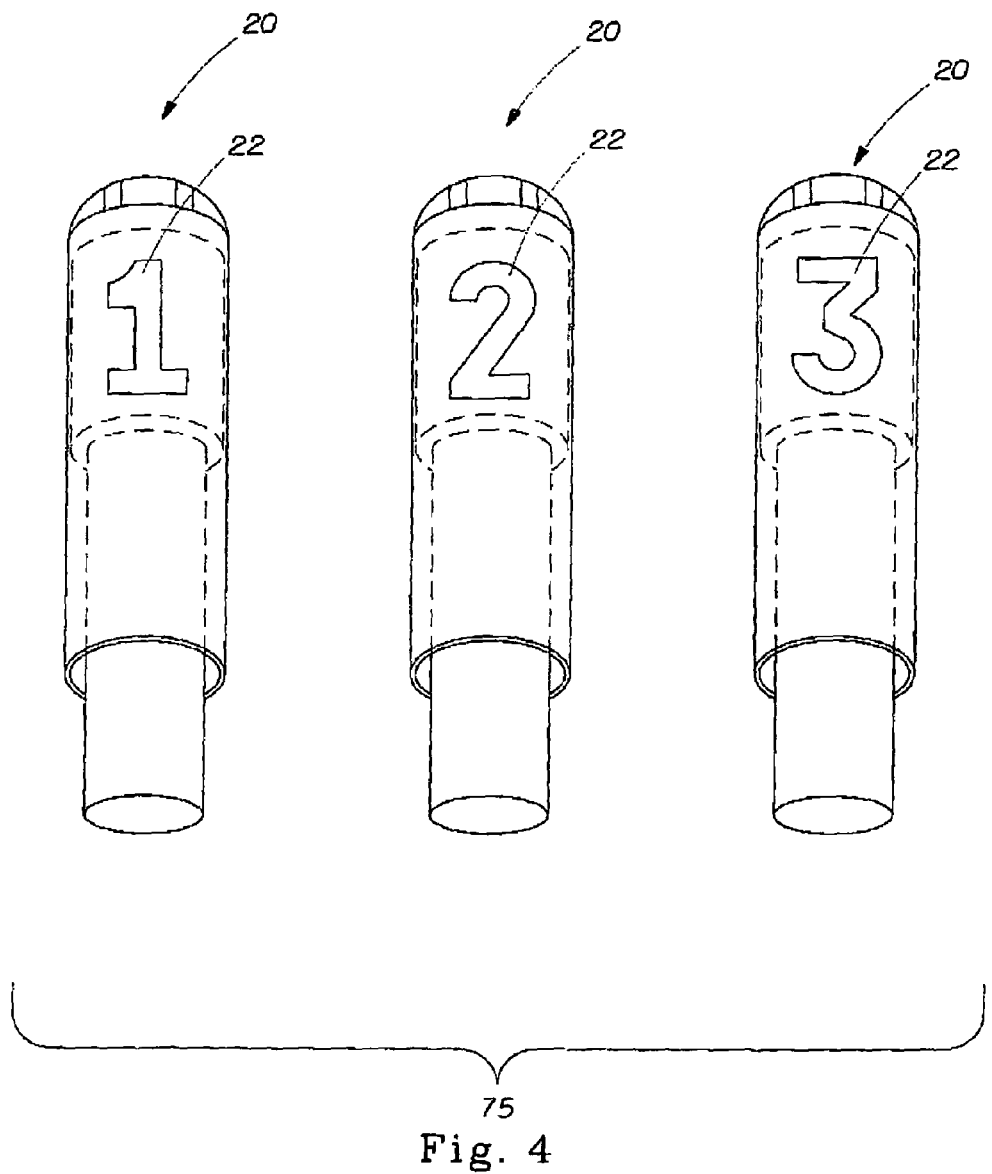
FIG. 4 is a view of an array of feminine hygiene articles of the present invention.

Referring to FIG. 4, the indicators 22 may encompass the entire tampon applicator 20 or may encompass part of the tampon applicator 20. For example, the indicators 22 may encompass one-fourth of the surface area of the tampon applicator 20. In yet another example, the indicators 22 may encompass two-thirds of the surface area of the tampon applicator 20.

The indicators 22 may be placed anywhere on the tampon applicator 20. In other words, the overall trade dress of the product may use the indicators 22 in a variety of ways. Specifically, the indicators 22 may be placed anywhere on the tampon applicator 20, e.g., on the top, sides, or bottom, or all three.

Referring to FIG. 4, the indicators 22 can be placed on the outer member 23, inner member 24, or on another portion of the tampon applicator 20 as long as it is visually perceptible to the user, or on any combination of the components of the tampon applicator 20.

Referring to FIG. 4, indicators 22 may be visually perceptible by techniques including, but not limited to, printing, stamping, coating, impregnating, embossing, folding, any known process that makes a visual, or even tactile, impression that indicates the indicator 22 having a surface area, or any combinations thereof. Various printing methods may be used to impart indicators 22 including, but not limited to, letterpress, flexography, gravure, offset lithography, screen, and inkjet. Indicators 22 can comprise printed indicia, such as ink-jet-printed figures, designs, lines or line segments, or embossed ridges or bumps, folds, pleats, or any other means known in the art for providing visible indications that impart an indictor 21 which covers the surface area of the tampon applicator 20 and aids the user in choosing the proper absorbency tampon from a line-up of tampon applicators.

Indicators 22 can be any size or shape. Indicators 22 can be any size as long as the indicator 22 is able to be readily perceived by a consumer without having to refer to an external basis or calibration means for comparison. The indicator 22 can be circular, square, rectangular, triangular, arced, curved, or any other conceivable shape possible as long as the indicator 22 is able to be readily perceived by a consumer without having to refer to an external basis or calibration means for comparison. While the indicators 22 can be a wide range of shapes, it is preferred to use a member selected from the group consisting of straight grooves, spiral grooves, flower petals, ellipses, and mixtures thereof.

The indicator(s) 22 may be formed to have essentially identical size and shape as compared to other indicators 22 on the individual tampon applicator 20. In one non-limiting example, the tampon applicator has twenty indicators shaped like protuberances. Each protuberance is identical to the other protuberances. Alternatively, the indicator 22 may be formed to have various sizes and shapes as compared to another indicator 22 on the tampon applicator 20. In one non-limiting example, the tampon applicator may have twenty indicators. However, each indicator may have a different geometric shape. Additionally, each indicator may have a different size.

The number of indicators 22 and the distance over which the indicators 22 extend may vary. The number of indicators 22 may range from about 1 to about 50. Either an even or an odd number of indicators 22 can be present. For ease of manufacturing, it is preferred that the indicators 22 be equally spaced relative to one another. The indicators 22, however, may be unequally spaced relative to one another.

The distance between each indicator 22 depends upon the area of the tampon 20 and the size and number of indicators 22.

Indicators 22 may be arranged randomly or in a pattern. For example, indicators 22 can be arranged to form any three-dimensional geometric pattern known including but not limited to diagonal lines, straight lines, checkerboard, flowers, ovals, circles, rectangles, trapezoids, triangles, cones, alphabet letters, and mixtures thereof. Alternatively, indicators 22 may be randomly arranged so that the multiplicity of indicators 22 may comprise merely a surface roughness in no apparent pattern. In addition, indicators 22 may be arranged such that the areas between the indicators 22 may form any geometric pattern known including but not limited to flowers, ovals, circles, rectangles, trapezoids, triangles, cones, alphabet letters, and mixtures thereof.

The indicator 22 may be formed to have essentially identical size and shape as compared to other indicators 22 in the same line-up. Moreover, while the use of increasing surface area, especially those having differing intensities, can be used to signal absorbency or other product performance characteristic such as size and strength, it is preferred to use differing surface areas which have indicators 22 of the same basic shape. For example, over the range of absorbencies: one groove which covers 10% of the surface area of the tampon applicator can signal light absorbency; two grooves which covers 30% of the surface area of the tampon applicator can signal regular absorbency; and three grooves which covers 60% of the surface area of the tampon applicator can signal extra absorbency.

Alternatively, the indicator 22 may be formed to have various sizes and shapes as compared to another indicators 22 in the same line-up. In other embodiments, the indicators 22 may have shapes which are not similar as long as the indicators 22 on each tampon applicator 20 have an increased surface area which correlates with the increased absorbency. An important advantage of using a range of surface areas within the line-up is that continuity for the visual selection of the overall product line is maintained, while the user is provided with the desired intuitive selection, and usage means which is the object of this invention.

Referring to FIG. 4, in another embodiment, feminine hygiene articles, such as tampons 20, can have indicators 22 that provide direct information-bearing signals to the user, such as numerals or written indicia that communicate information by way of clearly understood gradations in scale. For example, as shown in FIG. 4, an array 75 of tampon 20 can be identified by a number 1, with increasing numbers indicating an increase in a functional characteristic. For example, increasing numbers can signal an increasing amount of absorbent capacity relative to lower-numbered. As shown in FIG. 4, for example, the article on the far right numbered with the numeral "3" can have more absorbent capacity than that of the tampon 20 in the middle numbered with the numeral "2". Other indicators 22 could be used for a more aesthetic appearance.

Figure 5:
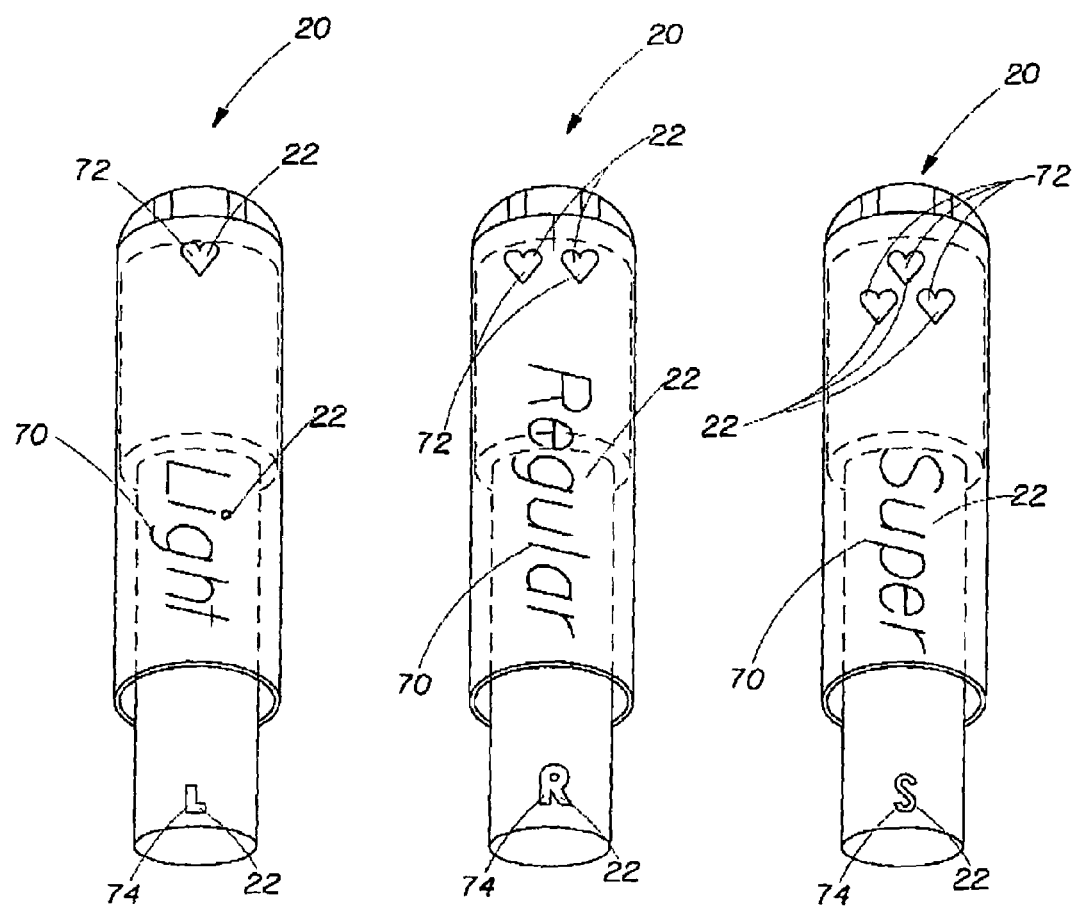
FIG. 5 is a view of an array of feminine hygiene articles of the present invention.

FIG. 5 shows an array 75 of tampon applicators 20 having a plurality of indicators 22. As shown, each tampon applicator 20 can have information-bearing written indicia 70 to literally "spell out" the functional characteristic, such as light absorbency, regular absorbency, or super absorbency capacity. In addition, or separately, an array of tampon applicators 20 can be differentiated by the number of visually distinct pattern elements 72 such as the heart shapes shown in FIG. 5. Thus, the greater number of hearts, the greater the characteristic signaled by the indicator 22. In addition, or separately, the indicator 22 can include a shortened form of the information-bearing written indicia 74, such as "L" for light absorbency, "R" for regular absorbency, and the "S" for super absorbency.

In each case of the embodiments of the present invention, one benefit to the user is the identification in an array of products of differing functional characteristics, the product or products the user can choose for her particular needs. Further, another benefit to the user is the ability to take visual notice after use of a product to identify the product for future use. Thus, a user may use the middle tampon applicator shown in FIG. 4, for example, and find that it is perfect for her needs. Upon removing the tampon applicator she has direct visual reinforcement as to which tampon applicator of all the various kinds it is. This enables her to easily replace it with a like tampon applicator without having to remember what kind of tampon applicator she used.

In a preferred mode, the product herein is displayed in a manner such that the consumer's attention is drawn to the entire product line. The product line may contain two or more products. Thus, on a store shelf or display rack, the products have the gradation of absorbencies preferably placed in a side-by-side array, most preferably in ascending order of absorbency. The ascending order may be from left to right; right to left; up to down; down to up; horizontally; or diagonally. It is noted that side-by-side herein means that all articles in the product line are in sufficient proximity to each other, either horizontally, vertically, or diagonally to be within the consumer's zone of perception at the same time. The products should be in close enough proximity to prevent undue confusion for the consumer. Thus, in a horizontal display reading from left-to-right, products having low absorbency (indicators covering less surface area), medium absorbency (indicators covering more surface area than the low absorbency tampon applicator but the indicators covering less surface area coverage than the high absorbency tampon), and high absorbency (indicators covering more surface area than the medium absorbency tampon applicator) are displayed together. This not only draws attention to the entire product line, but also provides additional visual signals to the consumer by virtue of the side-by-side display.

i. EXAMPLES

The following Example illustrates the practice of the invention, but is not intended to be limiting thereof.

Example I

The line-up consists of an array of tampon applicators comprising light, regular, and extra absorbency tampon applicators. Grooves 23 are indicators. In general, the greater the absorbency of the tampon, the indicator covers a greater surface area of the tampon applicator. The first tampon is a regular absorbency tampon which retains 6–9 grams. The regular absorbency tampon applicator has three sets of two grooves. The second tampon is a super absorbency tampon which retains 9–12 grams. This super absorbency tampon applicator has three sets of three grooves. The third tampon is a superplus absorbency tampon. The superplus absorbency tampon applicator has three sets of four grooves. Thus, this line-up of regular, super, and super-plus tampons consist of one indicator which varies in surface area to denote the respective absorbencies of the products within the kits.

Example II

The line-up consists of an array of tampon applicators having grooves as indicators comprising light, regular, and extra absorbency tampons. A regular absorbency tampon which retains 6–9 grams has grooves covering 20% of the surface area of the tampon applicator. A super absorbency tampon which retains 9–12 grams has grooves covering 40% of the surface area of the tampon applicator. A superplus absorbency tampon 27 which retains 12–15 grams has grooves covering 50% of the surface area of the tampon applicator.

Example III

A "multi-pack" kit comprising light, regular, and extra absorbency tampons can be prepared. These tampons are enclosed in their respective tampon applicators. The kit may consist of three tampon applicators having varying surface areas to denote the respective absorbencies of the products within the kits. The indicator is in the shape of a "T". The "T" is printed on the outer surface of the tampon applicator. The light tampon enclosed by the tampon applicator has 30% of the surface area of the tampon applicator covered by "Ts." The regular tampon enclosed by the regular tampon applicator has 60% of the surface area of the tampon applicator covered by "Ts." The extra absorbency tampon enclosed by extra absorbency tampon applicator has 90% of the surface area of the tampon applicator covered by "Ts."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of tampon applicators, said array comprising:
   a.) a first tampon applicator comprising
      i. an outer surface wherein said outer surface comprises an outer surface area and
      ii. a first identifier comprising a first surface area, wherein said first identifier is disposed on said first tampon applicator and corresponds to a first absorbency;
   b.) a second tampon applicator comprising
      i. an outer surface wherein said outer surface comprises an outer surface area and
      ii. a second identifier comprising a second surface area, wherein said second identifier is disposed on said second tampon applicator and corresponds to a second absorbency;
   c.) wherein said first surface area of said first tampon applicator being different than said second surface area of said second tampon applicator.

2. The array of claim 1 wherein said second surface area is greater than said first surface area.

3. The array of claim 1 wherein said second absorbency is greater than said first absorbency.

4. The array of claim 1 wherein said outer surface area of said second tampon applicator is the same as said outer surface area of said first tampon applicator.

5. The array of claim 1 wherein said first identifier is a shape and said second identifier is a shape.

6. The array of claim 5 wherein said shape of said first identifier is the same shape as said shape of said second identifier.

7. The array of claim 5 wherein said shape of said first identifier is a different shape than said shape of said second identifier.

8. The array of claim 5 wherein said shape of said first identifier and said second identifier comprises surface aberrations.

9. The array of claim 8 wherein said surface aberrations are selected from the group consisting of protuberances, depressions and mixtures thereof.

10. The array of claim 9 wherein said surface aberrations are arranged in a pattern.

11. The array of claim 10 wherein said pattern is selected form the group consisting of spiral lines, diagonal lines, straight lines, checkerboard and mixtures thereof.

12. The array of claim 1 wherein said absorbent article is selected from the group consisting of tampons, sanitary napkins, sanitary panties, interlabial devices, intravaginal devices, adult incontinence products, diapers, and pantiliners.

13. The tampon according to claim 12 wherein said tampon comprises fibrous material wherein said tampon has an essentially uniform density over a cross section of the tampon.

14. The tampon according to claim 12 wherein said tampon comprises fibrous material wherein said tampon has varying density over a cross-section of the tampon.

15. The tampon according to claim 12 wherein said tampon further comprises a core which is highly compressed.

16. The tampon according to claim 12 wherein said tampon comprises a withdrawal end wherein said withdrawal end further comprises a withdrawal member.

17. The tampon according to claim 12 wherein said tampon comprises a withdrawal end wherein said withdrawal end further comprises a finger indent.

* * * * *